United States Patent [19]

Matsumoto et al.

[11] Patent Number: 4,790,479

[45] Date of Patent: Dec. 13, 1988

[54] OSCILLATING CONSTRUCTION FOR AN ULTRASONIC ATOMIZER INHALER

[75] Inventors: Kazuhiro Matsumoto, Kyoto; Kei Asai, Osaka; Hirohito Yamamoto, Ohtsu, all of Japan

[73] Assignee: Omron Tateisi Electronics Co., Kyoto, Japan

[21] Appl. No.: 154,461

[22] Filed: Feb. 8, 1988

Related U.S. Application Data

[63] Continuation of Ser. No. 774,502, Sep. 10, 1985, abandoned.

[30] Foreign Application Priority Data

| | | | |
|---|---|---|---|
| Sep. 7, 1984 | [JP] | Japan | 59-188702 |
| Sep. 7, 1984 | [JP] | Japan | 59-136283[U] |
| Sep. 8, 1984 | [JP] | Japan | 59-136311[U] |
| Sep. 10, 1984 | [JP] | Japan | 59-137533[U] |
| Sep. 10, 1984 | [JP] | Japan | 59-139891[U] |
| Sep. 12, 1984 | [JP] | Japan | 59-192271 |

[51] Int. Cl.[4] .......... B05B 1/08

[52] U.S. Cl. .......... 239/102.2; 128/200.16; 261/81; 261/DIG. 48

[58] Field of Search ...... 239/102.2; 261/81, DIG. 48; 128/200.16

[56] References Cited

U.S. PATENT DOCUMENTS

| | | | |
|---|---|---|---|
| 3,346,189 | 10/1967 | Eisenkraft | 239/102.2 |
| 3,433,461 | 3/1969 | Scarpa | 239/102.2 |
| 3,648,929 | 3/1972 | Corbaz | 239/102.2 |
| 3,966,120 | 6/1976 | Furgalus et al. | 239/102.2 |
| 4,081,233 | 3/1978 | Kitajima et al. | 239/102.2 |
| 4,474,326 | 2/1984 | Takahashi . | |
| 4,479,609 | 10/1984 | Maeda et al. | 239/102.2 |
| 4,541,564 | 9/1985 | Berger et al. | 239/102.2 |

FOREIGN PATENT DOCUMENTS

| | | |
|---|---|---|
| 173334 | 5/1986 | European Pat. Off. . |
| 3202597 | 8/1983 | Fed. Rep. of Germany . |
| 2507807 | 12/1982 | France . |
| 807080 | 1/1959 | United Kingdom . |
| 2100896 | 6/1983 | United Kingdom . |

*Primary Examiner*—Douglas C. Butler
*Assistant Examiner*—Michael J. Forman
*Attorney, Agent, or Firm*—Wegner & Bretschneider

[57] ABSTRACT

This oscillating construction for an ultrasonic atomizing inhaler includes an oscillation element which is excited to vibrate ultrasonically, and this oscillation element has two adjoining regions which have substantially different vibrational characteristics. Liquid supply is made to one of the regions, and the oscillation for atomization takes place in the other region, according to the particular frequency of ultrasonic excitation of the oscillation element which is appropriately chosen. The region to which liquid is supplied has a resonance frequency which is different from that of the region for atomization, and substantially no atomization takes place in the liquid supply region. Therefore, even when the load imposed on the oscillation element by liquid thereon changes, as for example if the amount of the liquid thereon has changed, oscillation of a constant frequency continues in the atomization region, and thereby proper atomization is maintained. Thus, there is provided an ultrasonic atomizer which effects proper supply of liquid to be atomized, which does not cause oversupply or undersupply of liquid to be atomized, and which further can handle fluids of various different viscosities, including even quite viscous liquid, and is not wasteful of atomization liquid. Thus, this ultrasonic atomizer is not uneconomical during use. Further, it is not prone to dribbling of atomization liquid, and thus is not liable to cause a mess.

7 Claims, 16 Drawing Sheets

(a)

(b)

OSCILLATING CONSTRUCTION FOR AN ULTRASONIC ATOMIZER INHALER

This application is a continuation of U.S. patent application Ser. No. 774,502, filed Sept. 10, 1985, now abandoned.

BACKGROUND OF THE INVENTION

The present invention relates to the field of ultrasonic atomizing inhalers, and in particular to an improved oscillating construction for such an ultrasonic atomizing inhaler which improves on the prior art.

There are various types of ultrasonic atomizing inhalers; one of these typically has a horn construction for vibrating at an ultrasonic frequency and for atomizing liquid supplied thereto, and the atomized liquid drifts away from said horn construction and enters into the mouth and/or the nose of a user. Such an ultrasonic atomizing inhaler is typically used for the inhalation of liquid medicine, and for humidification of the larynx of the user.

The horn construction of a typical such ultrasonic atomizing inhaler is shown in FIG. 1*a* of the accompanying drawings in side view, and in FIG. 1*b* in an end on view. In this inhaler, the cone shaped horn construction e serves for concentrating ultrasound waves produced at its larger end a by the vibration of an ultrasonic oscillating element c which is driven by an oscillation circuit g, into its smaller end b, so as to vibrate an oscillating plate d integrally formed at its said smaller end b. A supply of liquid such as medicine is held in a storage bottle (not shown), and is picked up therefrom by a wick construction or absorptive bar f and is delivered little by little to the oscillating plate d by capillary action, whence it is atomized into the air by the vibrations of said oscillating plate d, to drift into the mouth and the throat and lungs of a user. And the horn construction b is held in place by a flange h which is connected to a main body (not shown) of the inhaler.

In such a conventional ultrasonic atomizing inhaler, the oscillation member such as the plate d is typically a circular plate or disk, and proper atomization is possible only when the oscillation frequency produced by the oscillation circuit g and the resonance frequency of the oscillation plate d are well matched, so that said plate d becomes excited. But, when the supply of liquid from the absorptive bar f or the load condition has changed, as for example when a more viscous liquid is being used for atomization than before, the resonance frequency of the oscillation plate d with the load of liquid thereon accordingly changes, whereby the atomization action is weakened. Also, by droplets which have not been atomized adhering to the atomization surface of the oscillation plate d and thereby causing overload, the power consumption for driving the oscillation circuit g can become increased, and the durability of the battery is thereby undesirably reduced. When the quantitative control of the liquid supply is not proper, droplets tend to build up on the atomization surface of the oscillation plate d, thereby causing over supply of liquid, and because the liquid is not properly atomized by the power of the device the droplets have to be removed by hand, which is a great inconvenience and is also wasteful of possibly expensive liquid such as costly medication. Also, in the worst case, these accumulated droplets could dribble down out of the atomizer, which would be very messy. Therefore, in order to accomplish proper atomization, it is necessary to properly control the liquid supply, but since the liquid supply unit (not shown) is often removed away from the atomization plate d of the horn e for supply and replenishing of liquid, the engagement between the liquid supply unit and the atomization plate d of the horn e tends to change every time they are put together, whereby it has been difficult to satisfy the above mentioned conditions. Accordingly, unsatisfactory atomization action has sometimes occurred with the prior art.

Another problem that has tended to occur with ultrasonic atomizing inhalers of this sort has related to particle size. The optimum particle size for inhalation of medication into the larynx varies according to the type of the medication and according to the exact point in the respiratory tract to which the medication is to be applied and to the symptoms of the patient, and in particular application of medication to the deep part of the trachea requires quite a different particle size for the atomized medication from that required by application to the shallow part of the larynx. Accordingly, it is desirable for an ultrasonic atomizing inhaler to be able to operate to atomize medication into particles of differing particle size. However, since the oscillation plate of the horn of a conventional ultrasonic atomizer is circular, it can have only one basic resonance frequency, and accordingly only can satisfactorily perform atomization at one frequency and at one particle size, with respect to a particular type of medication. Therefore, in order to change the average particle size of the atomized particles, it is necessary to prepare a plurality of ultrasonic atomizers (or, at least, horn assemblies) having different resonance frequencies.

Another problem that has tended to occur with ultrasonic atomizing inhalers of this sort has related to support of the horn assembly. Conventionally, the horn assembly has been supported within the main body of the inhaler in one of two ways. Either a flange has been integrally formed around the circumferential direction of the horn main body at a longitudinal position therealong corresponding to a node of the longitudinal oscillations thereof, said flange being coupled to said main body of said inhaler by its outer periphery being fitted into a groove therein (this structure is suggested in FIG. 1); or, alternatively, at said longitudinal position along the horn main body corresponding to a node of the longitudinal oscillations thereof, a circumferential groove has been formed, and the inner periphery of an annular retaining member has been fitted into this circumferential groove, the outer periphery of said annular retaining member being fitted into a groove in said main body of said inhaler.

However, the mass and the dimension of the horn of a typical such ultrasonic atomizing inhaler, and particularly of the horn of such an inhaler intended for home use, have become so small that, when an oscillation of frequency from 100 kHz to 300 kHz is to be produced in such a horn, although it may be possible in theory to compute an oscillation nodal point to be used as a support point, if a flange or groove is to be provided at said point as mentioned above, the dimensional precision of such a flange or groove must be very high. Accordingly, the machining process is caused to be very difficult, and accordingly the cost is raised. This problem has been a serious obstacle to providing an ultrasonic inhaler which is economical enough for home use. And, even with the utmost diligence, it is not practicable to support the horn assembly at a true nodal point at which the amplitude of the longitudinal oscillation is zero, and accordingly some elasticity in the support construction has been required. Furthermore, when such a flange or groove is formed in an extremely small horn for supporting it, effects from oscillation modes other than the longitudinal oscillation mode may be produced, and the atomization efficiency may be impaired.

Another type of problem that occurs with ultrasonic atomizing inhalers of this sort has related to electrical connection to the horn assembly. Typical schemes for connection to a conical type horn assembly and to a stepped type horn assembly are shown in FIGS. 12 and 13 of the appended drawings in side view: for the conical type horn assembly of FIG. 12, two lead wires 9*a* and 9*b* are soldered at their one ends to appropriate points on a circuit base board 8, and at their other ends, respectively, to an end surface of the ultrasonic oscillation element 3, and to a side wall 1 of the conical horn assembly. And, in a similar way, in the step type horn assembly of FIG. 13, two lead wires 20*a* and 20*b* are soldered at their one ends to appropriate points on a circuit base board 19, and at their other ends, respectively, to an end surface of the ultrasonic oscillation element 3, and to a side wall 11 of the step type horn assembly. But the problem arises with such a connection construction that, since the horn assembly is very small with the ceramic ultrasonic oscillation element thereon typically having a diameter of from 10 to 20 millimeters in diameter, the work of fixing such lead wires to the horn assembly, especially by soldering, has been very troublesome and prone to error.

Another type of problem that occurs with ultrasonic atomizing inhalers of this sort has related to heating up of the horn assembly. The temperature of the horn assembly rises sharply during the action of the ultrasonic oscillation element, and may attain a level close to 100° C. Therefore, such heating up could cause an averse effect in the adhesion portion between the horn assembly and the ultrasonic oscillation element, in the worst case causing peeling off of the ultrasonic oscillation element and damaging the oscillation capability of the horn assembly. In order to avoid this inconvenience, it might be considered desirable to provide a heat dissipation mechanism for the horn assembly, but, in a conventional ultrasonic atomizing inhaler of the sort described above, since the horn assembly has been supported on the main body case by a flange or by a groove, it has not been possible to provide a heat dissipation mechanism which can be guaranteed not to disrupt the oscillation of the horn assembly.

SUMMARY OF THE INVENTION

Accordingly, it is the primary object of the present invention to provide an oscillating construction for an ultrasonic atomizing inhaler which overcomes the above outlined problems.

It is a further object of the present invention to provide such an oscillating construction for an ultrasonic atomizing inhaler which always effects proper atomization of the liquid supplied, even when the load on said oscillating construction changes.

It is a further object of the present invention to provide such an oscillating construction for an ultrasonic atomizing inhaler which does not cause over supply or under supply of liquid to be atomized, and which can satisfactorily supply even viscous liquid.

It is a further object of the present invention to provide such an oscillating construction for an ultrasonic atomizing inhaler which is not prone to accumulation of non atomized droplets of atomization liquid.

It is a further object of the present invention to provide such an oscillating construction for an ultrasonic atomizing inhaler which is not wasteful of atomization liquid, or uneconomical during use.

It is a further object of the present invention to provide such an oscillating construction for an ultrasonic atomizing inhaler which is not prone to dribbling of atomization liquid, or to being messy.

It is a further object of the present invention to provide such an oscillating construction for an ultrasonic atomizing inhaler which can be easily replenished without any difficulties of adjustment.

It is a yet further object of the present invention to provide such an oscillating construction for an ultrasonic atomizing inhaler which can easily atomize liquid into mist of varying particle sizes, according to requirements.

It is a yet further object of the present invention to provide such an oscillating construction for an ultrasonic atomizing inhaler with particle size variation capability, without requiring any proliferation of parts.

It is a yet further object of the present invention to provide such an oscillating construction for an ultrasonic atomizing inhaler which does not impose any very severe manufacturing or machining requirements.

It is a yet further object of the present invention to provide such an oscillating construction for an ultrasonic atomizing inhaler which has a support mechanism for the horn structure thereof which does not very much affect the longitudinal vibrational mode of said horn structure.

It is a yet further object of the present invention to provide such an oscillating construction for an ultrasonic atomizing inhaler which does not require any high dimensional accuracy during manufacture, and which is economical to manufacture, accordingly being suitable for home use.

It is a yet further object of the present invention to provide such an oscillating construction for an ultrasonic atomizing inhaler in which provision of electrical connection to the ultrasonic oscillating element thereof is facilitated.

It is a yet further object of the present invention to provide such an oscillating construction for an ultrasonic atomizing inhaler which is capable of efficient heat dissipation, without deteriorating the oscillation capability of the oscillating construction.

According to the most general aspect of the present invention, these and other objects are accomplished by an oscillating construction for an ultrasonic atomizing inhaler, comprising an oscillation element which is excited to vibrate ultrasonically, wherein said oscillation element comprises two adjoining regions which have substantially different vibrational characteristics.

According to such a structure, liquid supply is made to one of the regions having substantially different vibrational characteristics, and the oscillation for atomization takes place in the other region, according to the particular frequency of ultrasonic excitation of the oscillation element which is appropriately chosen. The region to which liquid is supplied has a resonance frequency which is different from that of the region for atomization, and substantially no atomization takes place in the liquid supply region. Therefore, even when the load imposed on the oscillation element by liquid thereon has changed, as for example if the amount of the liquid on the liquid supply region thereof has changed, the oscillation of a constant frequency continues in the atomization region, and thereby proper atomization is maintained. Thereby, there is provided an ultrasonic atomizer which effects proper supply of liquid to be atomized, which does not cause oversupply or undersupply of liquid to be atomized, and which further can handle fluids of various different viscosities, including even quite viscous liquid, and is not wasteful of atomization liquid. Thus, this ultrasonic atomizer is not uneconomical during use. Further, it is not prone to dribbling of atomization liquid, and thus is not liable to cause a mess.

Further, according to a more particular aspect of the present invention, these and other objects are more particularly and concretely accomplished by an oscillating construction for an ultrasonic atomizing inhaler as described above, further comprising a means for exciting said oscillation element so as to cause it to vibrate ultrasonically, selectable to either of two different frequencies.

According to such a structure, when the oscillation means is selected to oscillate at one of the frequencies and the ultrasonic oscillation element is driven by it, one of the two regions corresponding to this frequency alone oscillates, so that atomization is performed by this region, but when the oscillation means is selected to oscillate at the other frequency, then accordingly the other region of the ultrasonic oscillation element oscillates, and this region performs the atomization action. Since the two regions of the oscillation element have different oscillation frequencies, the two regions can perform atomization to produce different particle diameters.

Further, according to a yet more particular aspect of the present invention, these and other objects are yet more particularly and concretely accomplished by an oscillating construction for an ultrasonic atomizing inhaler, comprising: a horn assembly, formed as a metallic unitary rigid body, having a major diameter end and a minor diameter end with an atomization portion formed thereon, and with a plurality of small holes formed around the circumferential direction of said horn assembly at points which are nodes with regard to longitudinal oscillation of said horn assembly; an ultrasonic oscillation element mounted on said major diameter end of said horn assembly; and a circlip the outer periphery of which is supported, with inwardly projecting portions which are engaged into said small holes to support said horn assembly.

According to such a structure, the horn assembly is supported at a plurality of points by the holes of the horn assembly and by the inwardly projecting engagement portions of the E ring. Therefore, the supporting means has very little influence on the longitudinal mode oscillation of the horn assembly, and further the machining work for the horn assembly during manufacture is simple, because all that is required is the drilling of these small holes in the horn.

Further, according to a yet more particular aspect of the present invention, these and other objects are yet more particularly and concretely accomplished by an oscillating construction for an ultrasonic atomizing inhaler comprising: a horn assembly, formed as a metallic unitary rigid body, having an atomization portion formed thereon and an ultrasonic oscillation element, remote from said atomization portion, mounted on a mounting portion thereof; wherein: a shaft portion is erected at a central portion of said mounting portion of said horn assembly integrally therewith, extending away from the direction of the atomization portion, and said ultrasonic oscillation element is fitted over said shaft portion and is securely attached to said mounting portion of said horn assembly, said shaft portion being supported by a base board of said inhaler so as to keep said base board and said ultrasonic oscillation element are mutually separated.

According to such a structure, since no flange or groove for support is required to be provided in the horn assembly main body, the horn assembly therefore becomes relatively simple in shape. As a result, machining becomes simpler and the adverse influences from a flange or groove on the oscillation mode are reduced. Furthermore, since the ultrasonic oscillation element may be attached to the horn assembly by fitting an annular hole formed in it over said shaft portion for guide action and then may be securely attached, positioning and adhesion of the ultrasonic oscillation element become relatively simple. Furthermore, one end surface of the ultrasonic oscillation element can be electrically connected to a base board by way of the shaft portion, which accordingly can additionally serve as an electrical connection member.

Further, according to a yet more particular aspect of the present invention, these and other objects are yet more particularly and concretely accomplished by an oscillating construction for an ultrasonic atomizing inhaler of the type proximately described, further comprising a heat dissipation member which is secured to said base board of said inhaler in substantial contact with said shaft member.

According to such a structure, the heat from the horn assembly is transmitted to the heat dissipation member for heat dissipation by way of the shaft portion of the horn assembly which is supported on the base board for supporting said horn assembly, thus without causing any ill effect on the oscillation of the horn assembly.

Further, according to a yet more particular aspect of the present invention, these and other objects are yet more particularly and concretely accomplished by an oscillating construction for an ultrasonic atomizing inhaler of the type described above, wherein said shaft portion at its one end contacts one of the electrodes of said ultrasonic oscillation element and at its other end contacts one side of an electrical circuit formed on said base board, thus electrically connecting said elements, and further comprising a springy member contacting the other side of said electric circuit on said base board by its one portion and contacting the other of the electrodes of said ultrasonic oscillation element by its another portion, thus electrically connecting said elements; and, optionally, said springy member may be securely fixed to said base board.

According to such a connecting structure for the ultrasonic oscillation element, since one of the electrodes of the ultrasonic oscillation element is connected to the circuit on the base board by way of the shaft portion, while the other electrode is connected to said circuit portion on the circuit base board by way of the springy contact member, no soldering is required to be made to the horn assembly itself, and the only requirement is to solder the contact member to the circuit base board. Thus, manufacture and assembly are simplified.

BRIEF DESCRIPTION OF THE DRAWINGS

The present invention will now be shown and described with reference to the preferred embodiments thereof, and with reference to the illustrative drawings. It should be clearly understood, however, that the description of the embodiments, and the drawings, are all of them given purely for the purposes of explanation and exemplification only, and are none of them intended to be limitative of the scope of the present invention in any way, since the scope of the present invention is to be defined solely by the legitimate and proper scope of the appended claims. In the drawings, like parts and spaces and so on are denoted by like reference symbols in the various figures thereof; in the description, spatial terms are to be everywhere understood in terms of the relevant figure; and:

FIG. 9*a* is an end on view, similar to FIG. 1*b* and so on, of an essential portion of an ultrasonic inhaler incorporating a sixth preferred embodiment of the present invention, and FIG. 9*b* is a side view thereof, similar to FIG. 1*a* and so on;

DESCRIPTION OF THE PREFERRED EMBODIMENTS

Figure 4:
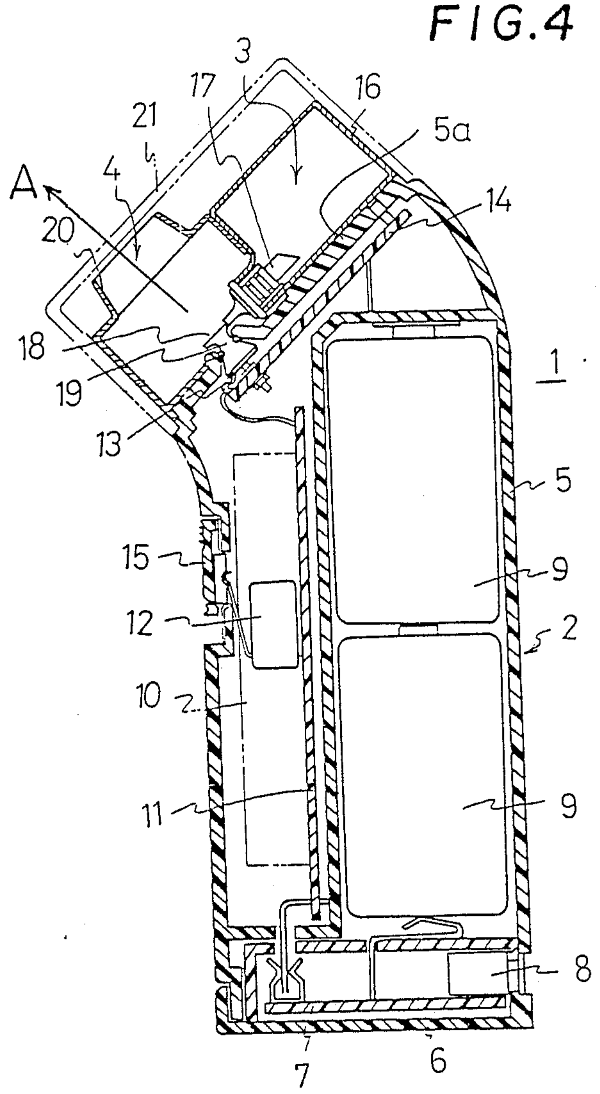
FIG. 4 is a longitudinal sectional view of said ultrasonic atomizing inhaler incorporating the first preferred embodiment of the present invention as a whole, taken in the same sectional plane as FIG. 2.

The present invention will now be described with reference to the preferred embodiments thereof, and with reference to the appended drawings. FIG. 4 is a longitudinal sectional view of an ultrasonic atomizing inhaler which incorporates the first preferred embodiment of the oscillating construction of the present invention. In this connection, reference should be made to copending U.S. patent application Ser. No. 153,467 filed Feb. 4, 1988, which is a continuation of Ser. No. 770,078 filed Aug. 28, 1985, now abandoned, the assignee of which is the same as the assignee of the present patent application, which describes and claims certain features of a similar type of ultrasonic atomizing inhaler. In this figure, the reference numeral 1 generally denotes the ultrasonic inhaler as a whole, and this is made up of a main body assembly 2, a liquid supply assembly 3, and an inhalation unit 4.

The main body assembly 2 defines the external contour of the ultrasonic inhaler, and comprises a main body casing 5 and a bottom plate 6. In the main body casing 5 there are housed a pair of batteries 9, 9 in a battery receiving portion thereof, and a power plug 8 with a power source circuit board 7 is further held within the main body casing 5 below said batteries 9, 9. The bottom plate 6 serves for closing the bottom of the main body casing 5 and for retaining the batteries 9, 9 and the power plug 8 therein. An oscillation circuit base board 11 is fitted parallel to the batteries 9, 9 at one side thereof, and bears an electronic circuit unit 10 including for example an oscillation circuit, as will be described later. A micro switch 12 is provided for controlling the apparatus, and is covered by a slidable switch cover 15. And a drive circuit base board 14 is provided at the top end of the main body 5, just below a top wall portion **5*a* thereof, for driving an oscillation element 13** which will be particularly described hereinafter.

On the other side of the top wall portion **5*a* are provided the liquid supply assembly 3 and the inhalation unit 4. When the ultrasonic inhaler is not in use, a hygienic cap 21, shown in FIG. 4 by double dotted lines only, covers both these assemblies. The liquid supply assembly 3, which will be discussed in greater detail later, comprises a storage bottle 16 for containing water or liquid medication and a liquid supply nozzle 17 fitted into said storage bottle 16 for allowing the controlled removal of liquid therefrom to the inhalation unit 4. The inhalation unit 4 comprises an inhalation nozzle 20 adapted to be approached to the nose and mouth of a user, and a horn unit 19 which has an oscillating atomization plate 18 integrally formed at the small end 32 of a rigid cone shaped portion 19*a* and an ultrasonic oscillation element 13 fitted at the larger end 31 of said rigid cone shaped portion 19*a*. The main body casing 5, the bottom plate 6, the switch cover 15, and the hygienic cap 21 are made of a material such as ABS resin, while the storage bottle 16, the liquid supply nozzle 17, and the inhalation nozzle 20** are made of a material such as styrene resin.

In detail, the horn unit 19 is mounted at the lower portion of the top wall portion **5*a* of the main body casing 5 of the ultrasonic inhaler, with the ultrasonic oscillating element 13 facing towards the inside and the oscillating atomization plate 18 facing outwards, and the inhalation nozzle 20 is detachably mounted to said top wall portion 5*a* over said horn unit 19 with its opening confronting the oscillating plate 18 and facing outwards. And the storage bottle 16 is detachably mounted at the upper portion of the top wall portion 5*a*, with the liquid supply nozzle 17 fitted thereinto substantially positioned at the lowest point thereof, and with the lower end of said liquid supply nozzle 17 positioned very close to the oscillating atomization plate 18** as will be explained hereinafter in detail.

Thus, when it is desired to use this ultrasonic inhaler 1, first the user—who has, as will be more particularly explained later in this specification, previously filled the storage bottle 16 with liquid such as water or medicine which is to be atomized and inhaled—removes the hygienic cap 21, and, after approaching his or her mouth and nose near the opening of the inhalation nozzle 20, switches ON the microswitch 12 by pushing appropriately on the switch cover 15. Thereby, the oscillation circuit of the electronic circuit unit 10 drives the ultrasonic oscillating element 13 of the horn unit 19 to oscillate at an ultrasonic frequency, as will be particularly described later, and this causes the atomization plate 18 to similarly oscillate with a considerable amplitude, due to the amplifying effect provided by the rigid cone shaped portion **19*a*. As will be explained shortly, a controlled supply of the liquid in the storage bottle 16 is provided to this atomization plate 18, and thus the vibration at ultrasonic frequency of the oscillation plate 18 atomizes this liquid into very minute droplets, which drift away from the atomization plate 18 in the direction indicated by the arrow A in FIG. 4 through the inhalation nozzle 20 to enter the mouth and nose of the user of the ultrasonic inhaler 1**, as desired, to provide medication and/or humidification of the user's larynx.

Figure 2:
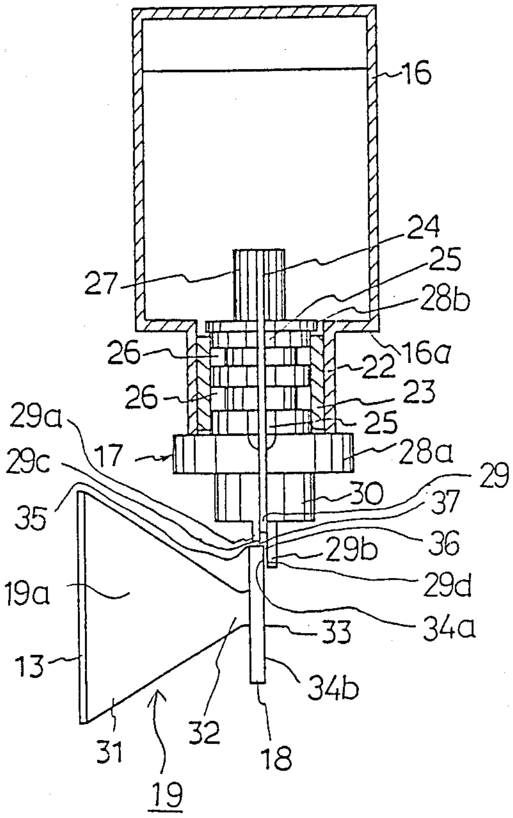
FIG. 2 is a sectional view relating to an ultrasonic atomizing inhaler incorporating the first preferred embodiment of the present invention, showing a bottle thereof, a nozzle thereof as fitted into said bottle, and a horn unit thereof properly positioned with respect to said bottle, thereto, as seen from the side.

Now, the detailed construction of the storage bottle 16, the liquid supply nozzle 17, and the horn unit 19 will be explained, with reference to FIGS. 2 and 3. In FIG. 2, there is shown a sectional view of the bottle 16, the nozzle 17 fitted thereinto, and the horn unit 19 taken in the same plane as in FIG. 4, but in enlarged scale; and FIG. 3 shows these parts as fitted to the top wall portion **5*a* of the main body casing 5**.

Figure 3:
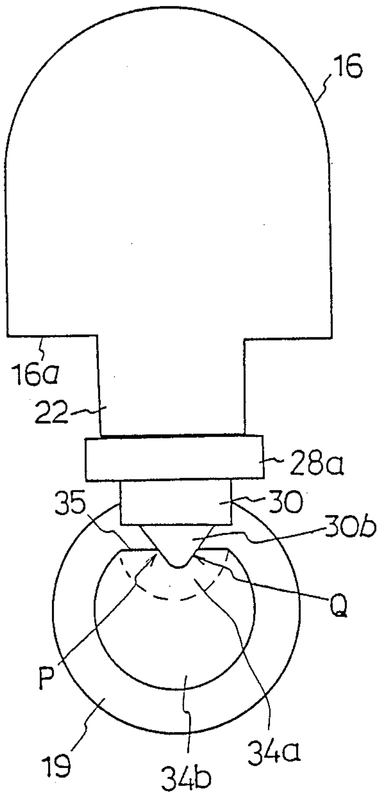
FIG. 3 shows these parts as fitted to the top wall portion of the main body casing of the ultrasonic inhaler.

The storage bottle 16 is shaped in an inverted U shape as seen from the front, as in FIG. 3, and further is shaped in a rectangular shape as seen from the side as in FIG. 3. As previously mentioned, the bottle 16 is formed from a transparent or translucent styrene resin. And from the bottom surface **16*a* of the storage bottle 16 there projects a tubular nozzle fitting member 22**.

Into this tubular nozzle fitting member 22 there is fitted the aforementioned liquid supply nozzle 17, with the interposition therebetween of a tube 23 made of a rubber like elastic material. This tube 23 is required to be somewhat distended, in order to be fitted over the nozzle 17, and further is then required to be somewhat compressed, in order for the nozzle 17 with said tube 23 fitted thereover to be fitted into the nozzle fitting member 22; accordingly, when this fitting has been accomplished, the inner cylindrical surface of the tube 23 is closely and sealingly contacted to the portions of the outer surface of the nozzle 17 with which it is in contact, and the outer cylindrical surface of said tube 23 is similarly closely and sealingly contacted to the inner cylindrical surface of the tubular nozzle fitting member 22. And thereby the nozzle 17 is securely held in said nozzle fitting member 22.

The form of the liquid supply nozzle 17 will now be explained. This nozzle 17 has a generally cylindrical shape, with a flange **28*a* formed near its one end 30 which is outside the storage bottle 16 and another smaller flange 28*b* formed near its other end 23 which is inside said storage bottle 16. The tube 23 is fitted between these two flanges 28*a* and 28*b* and is axially retained between them. And the larger lower flange 28*a* further serves for locating the nozzle 17 relative to the bottle 16, when said nozzle is fitted into the tubular nozzle fitting member 22 of said bottle 16. A plurality of circumferential grooves 26 (two in the shown construction) are formed as extending round the portion of the nozzle 17 between said two flanges 28*a* and 28*b*; and a pair of liquid supply grooves 24 extending in the axial direction of the nozzle 17, thus being orthogonal to the circumferential grooves 26, and spaced diametrically opposite from one another around said nozzle 17, are formed as cut quite deeply into the material of said nozzle 17; these liquid supply grooves 24 are extremely fine, for proper obtaining of capillary action as will be explained hereinafter, and function for leading liquid from the interior of the storage bottle 16 to the atomization plate 18 of the horn assembly 19. The circumferential grooves 26 are provided for forming temporary storage reservoirs for fluid which is being taken out from the storage bottle 16 through the liquid supply grooves 24, as will be explained in greater detail later. And through the two flanges 28*a* and 28*b* and through the flange portions remaining between the grooves 26 on either side thereof there are cut, superimposed upon the outer portion of the liquid supply grooves 24 and wider than said liquid supply grooves 24, two air supply grooves 25; these air supply grooves 25 are substantially wider than the liquid supply grooves 24, and function for leading air from the outside to the interior of the storage bottle 16. The end 27 of the liquid supply nozzle 17 inside the storage bottle 16 is quite long, and has the continued end portion of the liquid supply grooves 24 formed on it, thus appropriately leading said liquid supply grooves 24 well into the liquid inside said bottle 16. And, as best seen in the sectional view of FIG. 2, the lower end 30 of the liquid supply nozzle 17 is formed with two projecting end portions 29*a* and 29*b* separated by the two liquid supply grooves 24: the longer projecting end portion 29*b* is substantially longer than the other portion 29*a*, being formed in a substantially triangular shape, and its inside surface 29*d* is substantially planar; while the shorter projecting end portion 29*a* is cut off straight, having a substantially straight downwardly facing edge 29*c***.

The horn unit 19 comprises the rigid cone shaped portion **19*a*, and at the larger end 31 of said portion 19*a* is fitted the ultrasonic oscillation element 13. At the smaller end 32 of said rigid cone shaped portion 19*a* there is integrally formed the oscillating atomization plate 18, in an orientation perpendicular to the axis of said cone shape thereof; and this atomization plate 18 is in this first preferred embodiment of the present invention formed as a disk with a portion thereof defined by a chord 35 cut away, leaving the remainder 33 of its circumferential circle intact. Thus, the surface 34 of the plate 18 facing away from the cone shaped portion 19*a* is substantially planar. As best shown in FIG. 2, the horn unit 19 is so mounted to the top wall portion 5*a* of the main body casing 5, relative to the storage bottle 16, that this surface 34 of said atomization plate 18 confronts the aforementioned substantially planar inside surface 29*d* of the longer projecting lower end portion 29*b* of the liquid supply nozzle 17 with a certain very narrow gap 36 being defined therebetween. And, moreover, in this position the edge of the plate 18 defined by the chord 35 confronts the flat lower edge 29*c* of the shorter projecting end portion 29*a* of the liquid supply nozzle 17 with another very narrow gap 37** being defined therebetween.

Accordingly, it is seen that, in this first preferred embodiment of the present invention, the atomization plate 18 is formed with a boundary divided into two parts, which are generally at different distances from the center of said atomization plate 18. And the surface 34 of said atomization plate 18 can be considered as made up of two regions **34*a* and 34*b*: the region 34*a* is the one principally delimited by the chord line 35, while the other region 34*b* is the one principally delimited by the remainder 33 of the circumference of the disk shape of said atomization plate 18. The boundary between these two regions is necessarily conceptually vague, and it is accordingly indicated in FIG. 3** by a dashed line.

Thus, when the ultrasonic inhaler 1 as described above is being used, the atomization plate 18 is caused to vibrate at ultrasonic frequency as explained above; or, more exactly, the region **34*b* of said atomization plate 18, which is the one principally delimited by the remainder 33 of the circumference of the disk shape of said atomization plate 18, is caused to vibrate at high amplitude, since the frequency of the ultrasonic excitation provided to the ultrasonic oscillating element 13 by the oscillation circuit of the electronic circuit unit 10 is so chosen; but, since the region 34*a* of the atomization plate 18 which is principally delimited by the chord line 35** has a different fundamental frequency, it does not vibrate so much or with such a high amplitude.

At this time, liquid in the storage bottle 16 passes by the action of gravity and also by capillary action from the interior of said bottle 16, into the upper ends of the liquid supply grooves 24 where they are formed in the inwardly projecting portion 27 of the nozzle 17, and down through these grooves 24. The two circumferential grooves 26 define intermediate fluid reservoirs along this fluid flow path, said reservoirs being communicated to the sides of the grooves 24 at intermediate points therealong. Then the liquid flows to the outside of the bottle 16 down through the portions of the liquid supply grooves 24 formed in the outwardly projecting portion 30 of the nozzle 17, and therefrom flows to the surfaces **29*c* and 29*d* of the projecting end portions 29*a* and 29*b*, from which it flows across the narrow gaps 37 and 36 respectively, to the surface 34 of the atomization plate 18—in particular, to the region 34*a* thereof which is principally delimited by the chord line 35, and which, as explained above, is not vibrating with a very great amplitude. From this region 34*a*, the supplied liquid quickly creeps to the other region 34*b*, which is the one principally delimited by the remainder 33 of the circumference of the disk shape of said atomization plate 18, and which as explained above is vibrating at an ultrasonic frequency with a comparatively great amplitude. Then, as outlined previously, this liquid is atomized by the vibration at ultrasonic frequency of said portion 34*b* of the atomization plate 18, and drifts away from said plate 18 to pass through the aperture of the inhalation nozzle 20, in the direction indicated in FIG. 4 by the arrow A, to enter the mouth and nose of the user of the ultrasonic inhaler 1. Meanwhile, an amount of air substantially equal in volume to the amount of fluid thus taken out from the bottle 16 enters into the interior of said bottle 16 through the two air supply grooves 25. And since a relatively large volume of liquid may be satisfactorily supplied by the action of gravitation and by capillary action through the two liquid supply grooves 24, and since further reservoirs of liquid en route are provided by the circumferential grooves 26**, this supply of liquid to be atomized is performed smoothly and efficiently, according to the amount required, and interruption of liquid supply is never likely to occur.

During this liquid supply process, in fact mostly the liquid flows from the liquid supply grooves 24 onto the surface **29*d* of the longer projecting end portion 29*b* of the liquid supply nozzle 17, said end portion 29*b* being triangular in shape and the defining edge of its said surface 29*d* coming closest to the defining chord edge 35 of the above described non strongly vibrating region 34*a* of the oscillation plate 18 at two points P and Q (see FIG. 3). Then this liquid flows from this surface 29*d* over the gap 36 to said non strongly vibrating region 34*a* of the oscillation plate 18, principally around the two points P and Q, and accordingly is supplied to the strongly vibrating region 34*b* of the oscillation plate 18 from two directions, i.e. from the vicinities of said points P and Q. Since the liquid is thus supplied to substantially the whole circumference 33 of said strongly vibrating region 34*b* from these two directions, the area of the atomization plate 18** utilized for atomization is broadened. Furthermore, even when the conditions of liquid supply, such as the volume thereof, or the viscosity of the liquid and so on, at the non strongly vibrating region 34*a* of the oscillation plate 18 have changed, since this portion of the oscillation plate 18 does not substantially contribute to the atomization action for the liquid, no problems arise, and the oscillation of the strongly vibrating region 34*b* of said atomization plate 18 is not substantially influenced or affected. Therefore, even when the load imposed on the oscillation plate 18 by the liquid changes, the resonance frequency of the operative portion thereof, i.e. of the strongly vibrating region 34*b* thereof, is not substantially altered, and the atomization action can be maintained.

Now, when the ultrasonic inhaler 1 is switched off, with the atomization plate 18 not vibrating, then by the action of the surface tension of the liquid in the storage bottle 16 no undue supply of liquid from the bottle 16 can occur, and no improper dribbling of liquid can occur. This is further properly ensured by arranging that the liquid supply grooves 24 and the air supply grooves 25, as well as the circumferential grooves 26, are of appropriate dimensions in view of the surface tension and the viscosity, as well as possibly other characteristics, of the type of liquids to be used for atomization.

Figure 1:
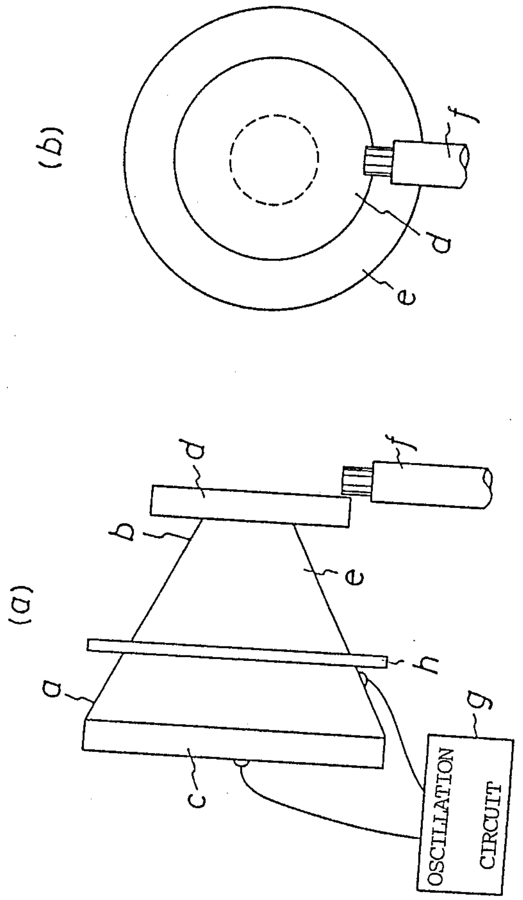
FIG. 1*a* is a side view of an essential portion of a conventional ultrasonic inhaler.
FIG. 1*b* is an end on view thereof.
Figure 5:
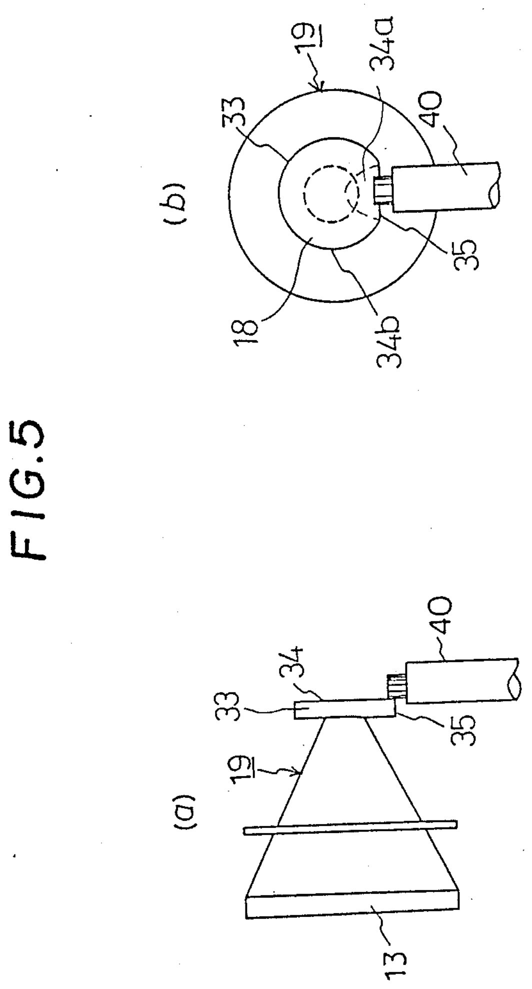
FIG. 5*a* is a side view, similar to FIG. 1*a*, of an essential portion of an ultrasonic inhaler incorporating the second preferred embodiment of the present invention.
FIG. 5*b* is an end on view thereof, similar to FIG. 1*b;*

Since by the shown construction for the ultrasonic inhaler and for the nozzle 17 the bottle 16 is positioned above the atomization unit 4, with the nozzle 17 at the bottom side of said bottle 16, not only is capillary action relied upon for performing liquid supply but also gravitational action is utilized, and thus there is no problem in supplying for atomization even the last few drops of the liquid contained in the bottle 16, which accordingly may satisfactorily be drained to its uttermost dregs. But this is not intended to be limitative of the present invention, and it would be possible, also, to supply the liquid to the region 34*a* of the atomization plate 18 which is principally delimited by the chord line 35 via a bottle located below said atomization plate by using an absorptive bar, in the general manner shown in FIG. 1 and discussed hereinabove. In fact, in FIGS. 5*a* and 5*b*, there are shown the horn assembly 19 and the liquid supply system relating to a second preferred embodiment of the present invention, in which this concept is implemented. In these figures, the orientation of the atomization plate 18 is opposite to the orientation of the corresponding atomization plate of the first preferred embodiment of the present invention as shown in FIGS. 2 and 3. In these figures, parts which correspond to parts of the first preferred embodiment shown in FIGS. 2 through 4 and discussed above, and which have the same functions, are denoted by the same reference symbols. The way in which this second preferred embodiment operates will be clear to one of ordinary skill in the ultrasonic atomizer art, based upon the disclosure hereinabove, and hence will not be expatiated upon. Again in this second preferred embodiment, the liquid is supplied, by an absorptive bar 40 this time, to a region 34*a* of the surface 34 of the atomization plate 18 which is principally delimited by the chord line 35, and which is not vibrating with a very great amplitude. From this region 34*a*, the supplied liquid quickly creeps to the other region 34*b*, which is the one principally delimited by the remainder 33 of the circumference of the disk shape of said atomization plate 18, and which as in the case of the first preferred embodiment is vibrating at an ultrasonic frequency with a comparatively great amplitude. Then, as outlined previously, this liquid is atomized by the vibration at ultrasonic frequency of said portion 34*b* of the atomization plate 18, and drifts away from said plate 18 to pass to enter the mouth and nose of the user of the ultrasonic inhaler 1. Accordingly, this second preferred embodiment of the present invention has the same advantages as outlined above with regard to the first preferred embodiment.

Figure 6:
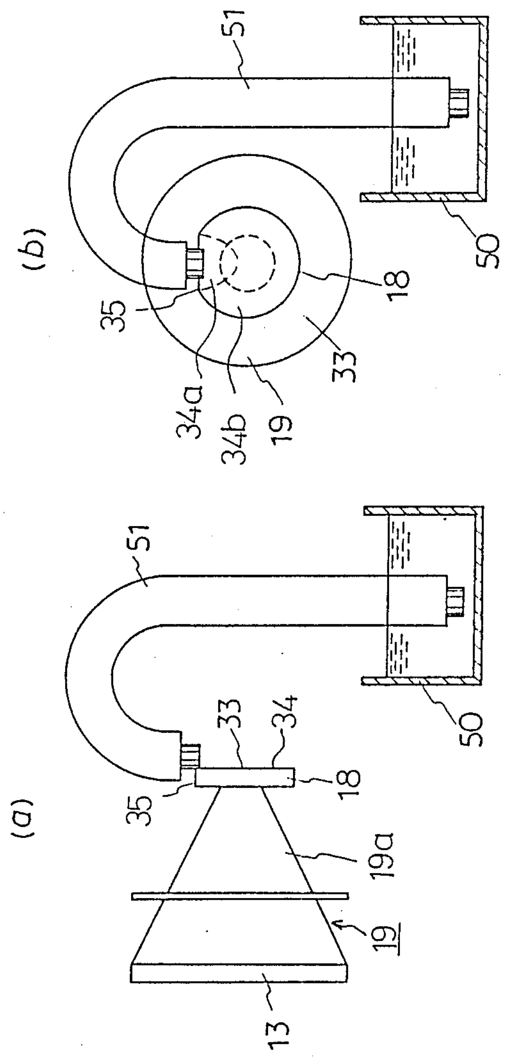
FIG. 6*a* is a side view, similar to FIGS. 1*a* and 5*a*, of an essential portion of an ultrasonic inhaler incorporating the third preferred embodiment of the present invention.
FIG. 6*b* is an end on view thereof, similar to FIGS. 1*b* and 5*b;*

In FIGS. 6*a* and 6*b*, there are shown the horn assembly 19 and the liquid supply system relating to a third preferred embodiment of the present invention. In these figures, the orientation of the atomization plate 18 is the same as the orientation of the corresponding atomization plate of the first preferred embodiment of the present invention as shown in FIGS. 2 and 3, and is opposite to that of the second preferred embodiment. In these figures, parts which correspond to parts of the first preferred embodiment shown in FIGS. 2 through 4 and discussed above, and of the second preferred embodiment shown in FIGS. 5*a* and 5*b*, and which have the same functions, are denoted by the same reference symbols. Again in this third preferred embodiment, the liquid is supplied, by an absorptive bar 51 this time which is shaped in an inverted J shape and leads said liquid by capillary action from a tank 50, to a region 34*a* of the surface 34 of the atomization plate 18 which is not vibrating with a very great amplitude. From this region 34*a*, the supplied liquid quickly creeps to the other strongly vibrating region 34*b*. Then, as outlined previously, this liquid is atomized and drifts away to enter the mouth and nose of the user. The way in which this third preferred embodiment operates will be clear to one of ordinary skill in the ultrasonic atomizer art, based upon the disclosure hereinabove, and hence will not be expatiated upon. Accordingly, this third preferred embodiment of the present invention has the same advantages as outlined above with regard to the first and second preferred embodiments.

Figure 7:
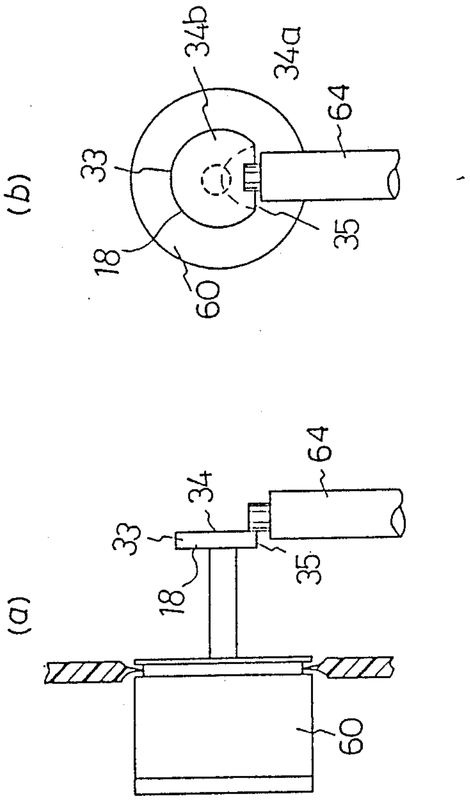
FIG. 7*a* is a side view, similar to FIGS. 1*a*, 5*a*, and 6*a*, of an essential portion of an ultrasonic inhaler incorporating the fourth preferred embodiment of the present invention.
FIG. 7*b* is an end on view thereof, similar to FIGS. 1*b*, 5*b*, and 6*b;*

In FIGS. 7*a* and 7*b*, there are shown the horn assembly 19 and the liquid supply system relating to a fourth preferred embodiment of the present invention. In this fourth preferred embodiment, the horn assembly is configured differently, being a stepped shape horn 60; however, the oscillating plate 18 is of the same type as in the first through the third preferred embodiments discussed above. In these figures, parts which correspond to parts of the first through third preferred embodiments shown in FIGS. 2 through 6 and discussed above, and which have the same functions, are denoted by the same reference symbols. Again in this fourth preferred embodiment, the liquid is supplied by an absorptive bar 64 to a region 34*a* of the surface 34 of the atomization plate 18 which is not vibrating with a very great amplitude. From this region 34*a*, the supplied liquid quickly creeps to the other strongly vibrating region 34*b*. Then, as before, this liquid is atomized and drifts away to enter the mouth and nose of the user. The way in which this fourth preferred embodiment operates will be clear to one of ordinary skill in the ultrasonic atomizer art, based upon the disclosure hereinabove, and hence will not be expatiated upon; and it has the same advantages as outlined above with regard to the first through the third preferred embodiments.

As a further possible modification of the present invention, although this is not shown in any of the above figures, it would be possible for the oscillation plate 18 to be formed as a rectangular m ember with long sides and short sides.

Thus, it is seen that, according to the horn oscillation unit of this invention, since the oscillation plate comprises two regions having different vibrational characteristics, and in the shown preferred embodiments having different distances between their edges and their center, by supplying liquid to one of the regions and producing atomization action in the other region, the fluctuations in the load imposed by the liquid do not affect the atomization action, whereby an ultrasonic atomizer which is immune to fluctuations in load can be obtained. Furthermore, since the liquid is supplied to the oscillation plate in two directions separately (from the regions around the points P and Q in FIG. 3), the oscillation surface of the oscillating plate is well utilized, and the atomization efficiency is improved.

Figure 8:
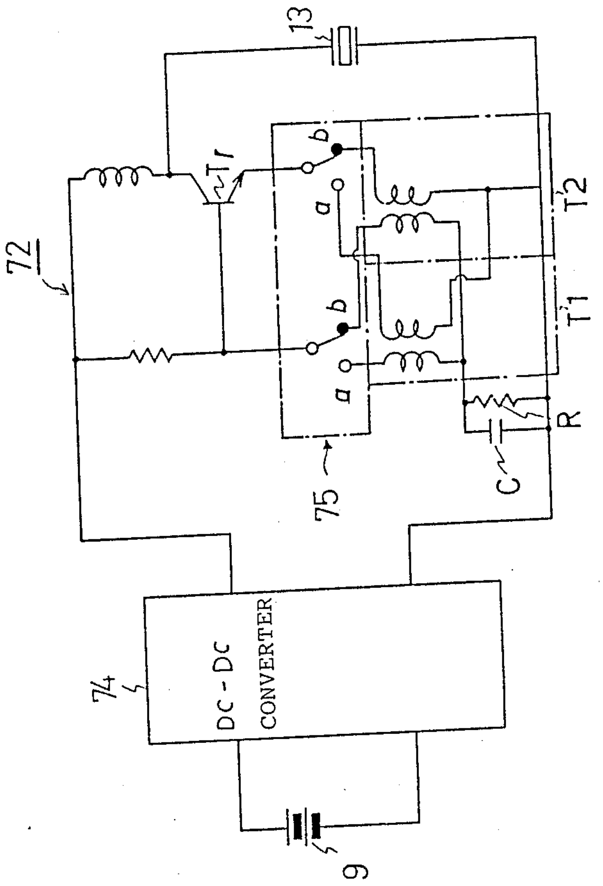
FIG. 8 is a circuit diagram for a drive circuit for driving an oscillation element, in a fifth preferred embodiment of the present invention.

Now, another aspect of the present invention will be discussed. FIG. 8 shows a circuit diagram for a drive circuit 72 on the base board 14 for driving the oscillation element 13, which is provided at the top end of the main body 5 just below the top wall portion 5*a* thereof, in a fifth preferred embodiment of the present invention; the remainder of this fifth preferred embodiment is like the first preferred embodiment shown above and described with reference to FIGS. 2 through 4, and hence will not be described in detail.

The voltage of the batteries 9 is raised by a DC - DC converter 74 and is supplied as a power source voltage to this drive circuit 72. The drive circuit 72 is a per se known type of blocking oscillator, and comprises a transistor Tr, a pair of transformers T1 and T2, a capacitor C, a resistor R, and so on, and by the action of a switch 75 it is possible to select one of the transformers T1 and T2 for use therein. In other words, depending upon whether the switch 75 is set to the a side or to the b side, one or the other of the transformers T1 and T2 of the oscillation circuit 72 is selected, and thus the oscillation circuit 72 can oscillate at two different frequencies. And the frequencies which may be switched over are designed so as to correspond to the resonance frequencies of the portion 34*a* of the oscillation plate 18 largely delimited by the chord 35 and the other portion 34*b* of said oscillation plate 18 largely delimited by the remainder 33 of the circumference of the disk shape thereof.

In this ultrasonic inhaler, when the switch 75 is set to the side a or to the side of the transformer T1, and the power is turned ON for starting oscillation for instance at the higher of the two frequencies, the ultrasonic oscillation element 13 oscillates at this higher frequency, and the ultrasonic waves thereby generated are transmitted through the main body 19*a* of the horn assembly 19 to the oscillation plate 18, causing the portion 34*a* thereof largely delimited by the chord 35 to vibrate strongly; and thus the liquid existing adjacent to said portion 34*a* is atomized. On the other hand, when the switch 75 is set to the side b or to the side of the transformer T2, the oscillation circuit 72 starts oscillating while connected to the transformer T2. If this oscillation frequency is lower than the one which was produced when the oscillation circuit 72 was connected to the side of the transformer T1, the ultrasonic oscillation element 13 oscillates at a frequency which is lower than the one which was produced when the switch 75 was selected to the side of the transformer T1. Accordingly, this time, the other portion 34*b* of said oscillation plate 18 largely delimited by the remainder 33 of the circumference of the disk shape of the oscillation plate 18 oscillates. And the liquid existing adjacent to this other portion 34*b* is atomized. And, since the resonance frequencies of the two portions 34*a* and 34*b* differ from each other, the resulting particle diameters of the atomized liquid also differ.

Although the horn was of a conical type in the above described fifth preferred embodiment, the concept thereof could be likewise implemented by using horns of other types, such as a step horn and so on. And, although the oscillation plate was defined into two regions having different resonance frequencies by cutting off a portion of a circular plate delimited by a chord in the above described embodiment, it is also possible to define the atomization portion with a rectangular shape having long sides and short sides, so as similarly to define two regions having different resonance frequencies. And, although in the above described embodiment supply of liquid to the atomization portion was made by an absorptive band, it is also possible to use other means such as a liquid supply nozzle and so on.

Thus, according to this aspect of the present invention, since atomization in different particle diameters is possible by a simple switch over of a switch, thereby one unit of the ultrasonic inhaler can perform the treatment of both the deep part of the trachea and the shallow part of the larynx, according to the current medical requirements, and the present invention can further be adapted to a wide variety of medications.

Figure 9:
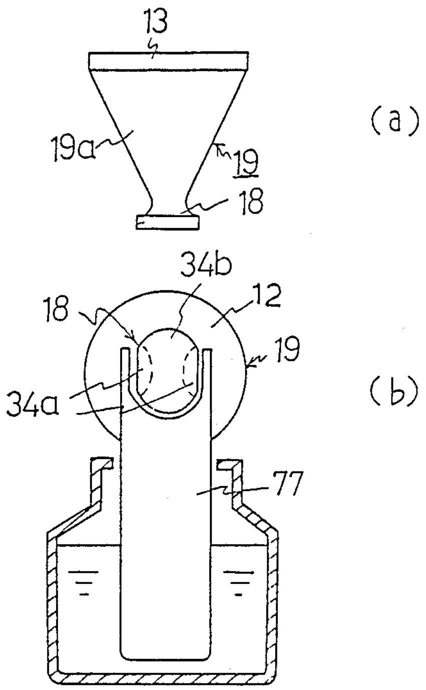

Further, in FIG. 9*a* there is shown a side view, and in FIG. 9*b* there is shown an end on view, of a sixth preferred embodiment of the present invention; again, like parts are denoted by like reference numerals. This structure is intended for use with a two frequency type of drive circuit 72 like that of FIG. 8, and differs from the previous ones in that the oscillation plate 18 is formed as a disk shape with two diametrically opposite portions cut away by two chords, so as to define two portions 34*a* thereof largely delimited by the chord 35 which tend to vibrate at one characteristic frequency and one intermediate portion 34*b* of said oscillation plate 18 largely delimited by the remainder 33 of the circumference of the disk shape thereof which tends to vibrate at the other characteristic frequency. The effects and advantages are the same as in the fifth preferred embodiment described above, and hence detailed discussion thereof will be omitted.

Figure 10:
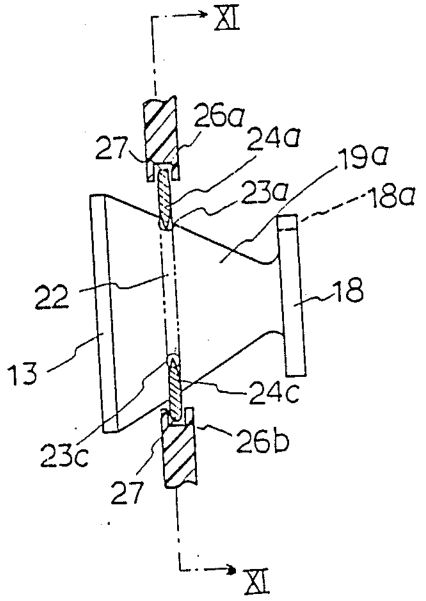
FIG. 10 is a schematic partly sectional side view of the horn assembly and of the support construction therefor, in a seventh preferred embodiment of the present invention.
Figure 11:
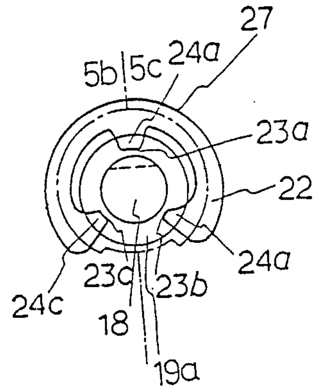
FIG. 11 is a sectional view of these portions of this seventh preferred embodiment taken in a plane indicated by the arrows XI—XI in FIG. 10.
Figure 12:
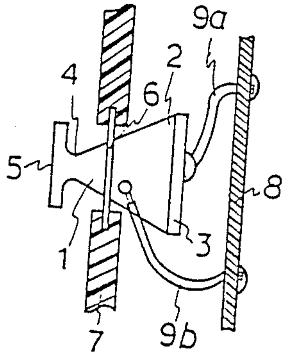
FIG. 12 is a side view of an essential portion of another conventional ultrasonic inhaler, particularly showing the electrical connection arrangements thereto.
Figure 13:
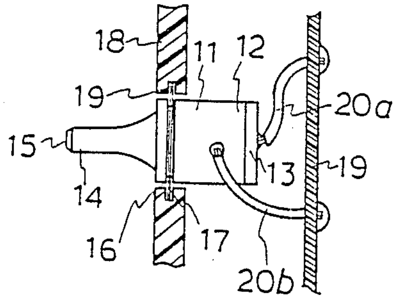
FIG. 13 is a side view of an essential portion of another conventional ultrasonic inhaler.

Now, in FIG. 10, there is shown a schematic partly sectional side view of the horn assembly 19, and of the support construction therefor, in a seventh preferred embodiment of the present invention; in this construction, like parts to parts in the previous embodiments are not necessarily denoted by like reference numerals. And, in FIG. 11, a sectional view of these portions of this seventh preferred embodiment taken in a plane indicated by the arrows XI—XI in FIG. 10 is shown. The support construction for the horn 19 in this embodiment of the present invention will now be described.

Three small holes 23*a*, 23*b*, and 23*c* are formed around the body 19*a* of the horn assembly 19 spaced apart at intervals of about 120° in the circumferential direction, at a longitudinal position therealong which corresponds to a nodal point of the longitudinal oscillation of said horn assembly 19. And inwardly projecting engagement portions 24*a*, 24*b*, and 24*c* of an E ring or circlip 22 are respectively engaged with these small holes 23*a*, 23*b*, and 23*c*. The upper wall portion 5*a* of the main body case 5 of the ultrasonic inhaler (see FIG. 4) is divided into two case halves 5*b* and 5*c*, and each half is provided with a groove 26*b* and 26*c* respectively of a semi circular shape for supporting the outer periphery 27 of the E ring 22. Thus, when the two case halves 5*b* and 5*c* are joined together from left and from right, the grooves 26b and 26c accomodate the outer edge 27 of the E ring 22 and the case halves 5a and 5b thus snugly hold the E ring 22. By this holding of the E ring 22 which itself is supporting the horn assembly 19, said horn assembly 19 is supported from the main body case 5 (5b and 5c) by way of this E ring 22.

The upper part and the lower part of each of the grooves 26a and 26b of the main body case halves 5b and 5c are made asymmetrically so as to be adapted to the shape of the E ring 22, and if the E ring 22 is positioned in an inverted orientation said E ring 22 cannot be properly fitted into the grooves 26 and 26. Therefore, when the small holes 23a, 23b, and 23c of the horn 19 are engaged to the engagement pieces 24a, 24b, and 24c of the E ring 22, once the E ring 22 is properly fitted into the grooves 26a and 26b of the main body case 26, the horn 19 is definitely guaranteed to be properly positioned and supported on the main body case 5. If the oscillation plate 18 is provided with a cut away portion 18a as indicated by a broken line, as in the previously outlined embodiments of the present invention, it becomes possible to align the cut away portion 18a properly with the liquid supply nozzle 17 (not shown, but as described above) by means of the above mentioned positioning means, thus obtaining a great constructional advantage.

Thus, according to the support mechanism for the horn assembly 19 according to this aspect of the present invention, because the horn assembly 19 is supported at three points by the three small holes of the horn main body 19a and by the three corresponding projections on the E ring, as compared to the case in which a conventional flange or groove is used for support, the load imposed on the longitudinal oscillation mode of the horn assembly 19 is reduced, and the consequent influence on the acoustic properties and the impedance properties of said horn assembly 19 is reduced, so that the atomization efficiency may be increased. Since it is only necessary to drill small holes in the horn assembly 19, the machining is simple, and it becomes possible to provide an ultrasonic atomizer which is economical as a whole.

Figure 14:
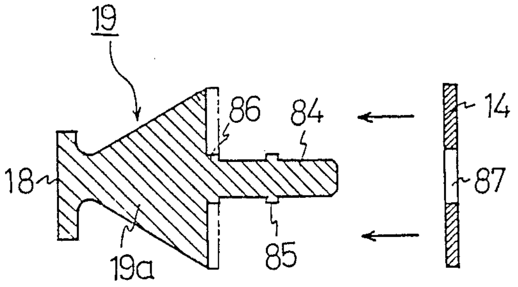
FIG. 14 is a schematic sectional view of the horn assembly and of the support construction therefor, in an eighth preferred embodiment of the present invention.

Now, in FIG. 14, there is shown a schematic longitudinal sectional view of the horn assembly 19, and of the support construction therefor, in an eighth preferred embodiment of the present invention; in this construction, like parts to parts in the previous embodiments are not necessarily denoted by like reference numerals. And, in FIG. 15, a sectional view of these portions of this eighth preferred embodiment as fitted to the base board 14 of the ultrasonic atomizing inhaler and thus mounted is shown. The support construction for the horn assembly 19 in this embodiment of the present invention will now be described.

The main body of the horn assembly 19 is made as a metallic rigid body, and has a conical shape as in previous embodiments. Its minor diameter end is provided with an atomization plate 18, while a central portion of its major diameter end is provided with a shaft portion 84 which projects in a direction opposite to the atomization plate 18. A middle portion of this shaft portion 84 is provided with a flange 85 for positioning the horn assembly 19 when supporting the horn assembly 19 on the base board 14 of the drive circuit for the ultrasonic inhaler, and a step portion 86 which has substantially the same diameter as this flange 85 is provided at the base end of this shaft portion 84, abutting the major diameter end of the horn assembly 19.

Figure 15:
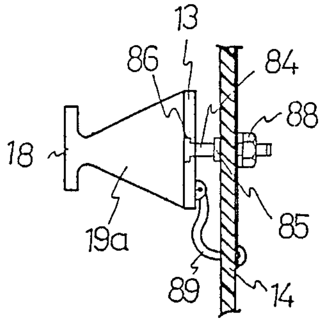
FIG. 15 shows a side view of said horn assembly as fixed to a base board.

As shown in FIG. 15, when the ultrasonic oscillation element 13 is to be attached to the end surface of the major diameter portion 83 of the horn assembly 19, since the ultrasonic oscillation element 13 is formed in an annular shape, by passing the shaft portion 84 through its central hole 87 the shaft portion 84 may guide the ultrasonic oscillation element 13 so that the ultrasonic oscillation element 13 may be adhered to an end surface of said major diameter end of the horn assembly 19 in proper alignment. When the horn assembly 19 with the ultrasonic oscillation element 13 thus securely adhered thereto is to be mounted on the circuit base board 14, the shaft portion 84 is passed through a hole in the circuit base board 14 from the left hand of the base board 14 and, when the flange 45 engages the base board 14, the horn assembly 19 is secured by fastening a nut 88 on the screw threaded projecting end of said shaft portion 84. By the above described process, one of the electrodes, i.e. the left electrode as seen in FIG. 14, of the ultrasonic oscillation element 13 is connected to a point of the electrical pattern printed on the circuit base board 14 by way of the shaft portion 84 of the horn assembly 19. Therefore, for connection of one of the terminals of the ultrasonic oscillation element 13, no lead wire is required. The other terminal of said ultrasonic oscillation element 13 is connected to another point of said wiring pattern by way of a lead wire 89 by soldering. The horn assembly 19 may be supported on the main body case of the ultrasonic inhaler by way of a cushion ring made of rubber or the like fitted at a nodal point thereof.

Figure 16:
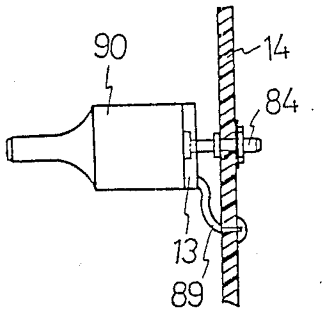
FIG. 16 is a side view of an essential portion of the horn assembly and of the support construction therefor, in a ninth preferred embodiment of the present invention.

FIG. 16 shows the case in which the horn assembly 19 is step shaped, as opposed to the conical horn assembly 19 of FIG. 14, and this ninth preferred embodiment is supported in substantially the same way as that of FIG. 14 and 15. Thus, according to the support mechanism for the horn assembly according to these preferred embodiments of the present invention, since the shaft portion acts as a guide when mounting the ultrasonic oscillation element to the horn assembly, and guides the ultrasonic oscillation element by its annular hole, the ultrasonic oscillation element may be adhered with a proper positioning to the horn assembly, and accordingly misalignment of the oscillation element may be avoided. Further, since the horn assembly according to these embodiments of the present invention does not require any flange or groove to be formed in the side wall of the main body of said horn assembly for support, the shape of said main body of said horn assembly is simplified, and through improved facility of machining a horn assembly of high precision may be obtained. And, since the shaft portion for supporting the horn assembly can be used also as one of the lead wires for driving the ultrasonic oscillation element, thereby the means such as a partition for supporting the horn oscillation unit and the circuit base board may be consolidated into one. Further, normally a horn assembly of the above type is made of stainless steel in consideration of corrosion resistance and pressure resistance, and conventionally soldering on such a horn assembly has not been well controllable in terms of the quantity of solder used, thereby giving rise to various problems of quality control. However, this point is also improved upon, according to this invention.

Figure 17:
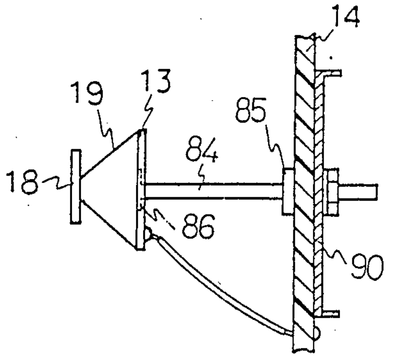
FIG. 17 is a schematic longitudinal sectional view of the horn assembly, and of the support construction therefor, as fitted to the base board of the ultrasonic atomizing inhaler and thus mounted, in an tenth preferred embodiment of the present invention in which a heat dissipation fin is provided.

Now, in FIG. 17, there is shown a schematic longitudinal sectional view of the horn assembly 19, and of the support construction therefor, as fitted to the base board 14 of the ultrasonic atomizing inhaler and thus mounted, in an tenth preferred embodiment of the present invention; in this construction, like parts to parts in the previous embodiments are not necessarily denoted by like reference numerals. The support construction for the horn assembly 19 in this embodiment of the present invention will now be described.

The main body of the horn assembly 19 is conical in shape as in many of the previous embodiments, and its minor diameter end is formed with the atomization portion 18, while a central portion of its major diameter end is provided with a shaft portion 84 which projects away from the atomization portion 18 in a projecting manner. A step portion 86 is provided in the base portion of this shaft portion 84, and a flange 85 of substantially the same diameter as said step portion 86 is formed at an intermediate position on the shaft portion 84. The annular shaped ultrasonic oscillation element 13 is fitted over the shaft portion 84 and is adhered to an end surface of the major diameter end of the horn assembly 19. And the shaft portion 84 is fitted through a hole provided in the base board 14 and is fixedly secured to the base board 14 with the flange 85 and a screw 87 clamping said base board 14 between them. At the same time as fixedly securing the horn 19 to the base board 14, a fin 90 for heat dissipation is fixedly secured by the screw 87 to the shaft portion 84, on the other side of said base board 14 from the horn assembly 19.

With the ultrasonic inhaler incorporating this horn assembly, when the action is started and the ultrasonic oscillation element 13 starts oscillation, its oscillation energy is transmitted through the main body of the horn 19 and is concentrated on the atomization portion 18 for atomization action. When the horn 19 becomes hot from this oscillation, the heat is efficiently dissipated to the space in the main body casing from the fin 90 by way of the shaft portion 84. Therefore, rising of the temperature of the horn assembly 19 is controlled, and peeling off of the ultrasonic oscillation element 13 from the horn assembly 19 is avoided.

Figure 18:
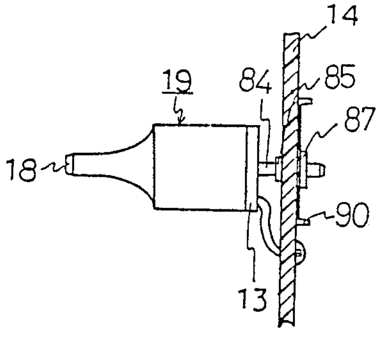
FIG. 18 is a similar figure to FIG. 17, showing an eleventh preferred embodiment, in which a step shaped horn assembly is supported instead of the conical horn assembly of the tenth preferred embodiment shown in FIG. 17.

FIG. 18 is a drawing showing an eleventh preferred embodiment, in which a step shaped horn assembly 19 is supported instead of the conical horn assembly 19 of the tenth preferred embodiment shown in FIG. 17, and this embodiment does not differ from the one shown in FIG. 17, except in that the shape of the horn assembly 19 is different.

Figure 19:
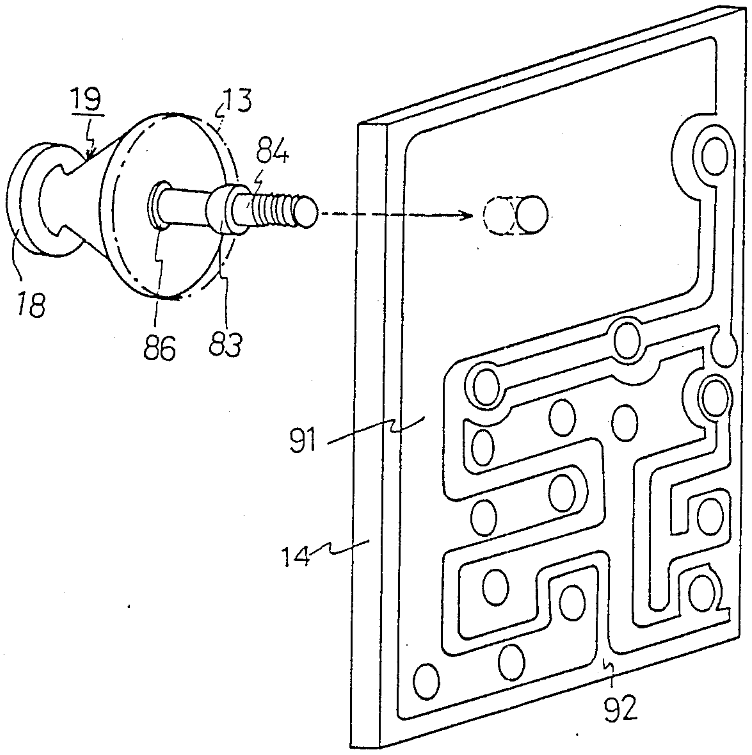
FIG. 19 is a schematic perspective view showing a twelfth preferred embodiment of the present invention, in which a portion of the ground wiring metallic layer of the wiring pattern formed as a printed circuit on the base board is utilized as the heat dissipation member.

Although in the above described embodiment a fin 90 was used as the heat dissipation member, it is also possible to use a portion of the ground wiring metallic layer 91 of the wiring pattern 92 formed as a printed circuit on the base board 14 as the heat dissipation member; this is schematically shown in perspective view, as the twelfth preferred embodiment of the present invention, in FIG. 19 in perspective view. By doing so, without providing any special fin for heat dissipation, a very high heat dissipation efficiency may be obtained, because the whole pattern of the ground wiring metallic layer 30 can be used as a heat dissipating surface.

Thus, according to the ultrasonic atomizer of this aspect of the present invention, since heat dissipation is performed by the heat dissipating member which is supported on the base board, by way of the shaft portion, without providing the heat dissipation member directly on the horn assembly main body and without thus disrupting the oscillation of the horn assembly, the horn assembly is well cooled and the durability of the oscillation construction may be extended.

Figure 20:
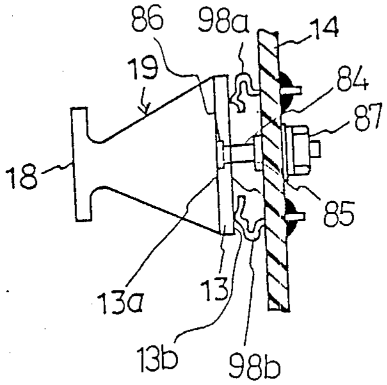
FIG. 20 is a schematic longitudinal sectional view of the horn assembly and of the support construction therefor, as fitted to the base board of the ultrasonic atomizing inhaler and thus mounted, in a thirteenth preferred embodiment of the present invention.

Now, in FIG. 20, there is shown a schematic longitudinal sectional view of the horn assembly 19, and of the support construction therefor, as fitted to the base board 14 of the ultrasonic atomizing inhaler and thus mounted, in an thirteenth preferred embodiment of the present invention; in this construction, like parts to parts in the previous embodiments are not necessarily denoted by like reference numerals. The support construction for the horn assembly 19 in this embodiment of the present invention will now be described.

The horn assembly 19 is made as a metallic rigid body as in previous embodiments, and its minor diameter end is integrally formed with an atomization portion or oscillation plate 18, while a central portion of its major diameter end has a shaft portion 84 which projects away from the atomization portion 18 or towards the circuit base board 14. A middle portion of this shaft portion 84 is provided with a flange 85 for positioning the horn 19 when supporting it on the base board 14, and a step portion 86 of the same diameter as the flange 85 is provided in the base portion of the shaft portion 84.

The ultrasonic oscillation element 13 which is annular in shape is fitted over the shaft portion 84, and one of its electrodes **13*a* is adhered and electrically connected to the end surface of the major diameter end of the horn 19. The shaft portion 84 is fixedly secured to the circuit base board 14 by the flange 85 and the nut 87 and is thus electrically connected to a grounding wire portion of the wiring pattern or printed circuit formed on the circuit base board 14. Thereby, one of the electrodes 13*a* of the ultrasonic oscillation element 13** is connected to the minus side of an appropriate electrical circuit.

By the shaft portion 84 being supported on the circuit base board 14, the horn assembly 19 is supported by the main body of the ultrasonic inhaler without said horn assembly 19 being disturbed with regards to its oscillation which is necessary for proper atomization performance.

Contact pieces **98*a* and 98*b* are soldered to the plus side of said electrical circuit on the circuit wiring pattern on the circuit base board 14, for applying positive voltage to the other electrode 13*b* of the ultrasonic oscillation element 13, and these contact pieces 98*a* and 98*b* contact said other electrode 13*b* of the ultrasonic oscillation element 13** by their inherent springiness and convey electricity thereto.

Thereby, the ultrasonic oscillation element 13 is connected to the positive and negative circuit portions of the circuit base board 14 by the contact pieces **98*a* and 98*b* and the shaft portion 84, and accordingly the ultrasonic oscillation element 13 is connected to the printed circuit on the circuit base board 14 without any lead wire requiring to be soldered to the ultrasonic oscillation element 13 or to the the horn assembly 19**.

Figure 22:
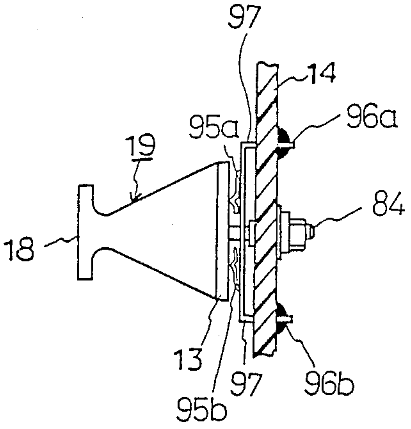
FIG. 22 is a sectional view of said fourteenth preferred embodiment, similar to FIG. 20 relating to the thirteenth embodiment.
Figure 21:
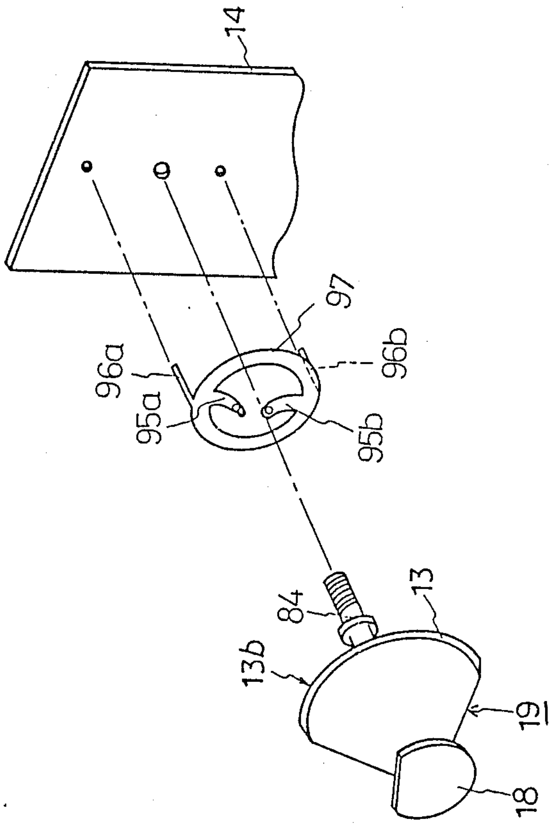
FIG. 21 is an exploded perspective view of said thirteenth preferred embodiment horn assembly and of the support construction therefor, also showing said base board.

Although in the above described thirteenth preferred embodiment separate springy contact pieces **98*a* and 98*b* were used for connecting the printed circuit on the circuit base board 14 to the ultrasonic oscillation element 13, the shape of the contact pieces need not be necessarily limited by this, and it is also possible to use a pair of contact pieces 95*a* and 95*b* which are formed as extending from a ring shaped base 97 of an annular shape to contact the other electrode 13*b*, while the ring shaped base 97 itself is soldered to the circuit base board 14 by way of its legs 96*a* and 96*b*. This is shown as the fourteenth preferred embodiment of the present invention in FIG. 21, which is an exploded perspective view of the horn assembly 19 and of the support construction therefor as fitted to the base board 14 of the ultrasonic atomizing inhaler and thus mounted, and in FIG. 22, which is a sectional view similar to FIG. 20** relating to the thirteenth embodiment.

As described above, according to the connecting mechanism for an ultrasonic oscillation element as shown in these preferred embodiments of the present invention, since the ultrasonic oscillation element is connected to the circuit base board by way of the horn assembly shaft portion and the contact pieces, as opposed to the conventional case in which direct soldering is made to the side surface of the horn assembly and/or to the electrodes of the ultrasonic oscillation element, soldering to the circuit base board is extremely simple, and the work required to electrically connect the ultrasonic oscillation element to the electric circuit becomes extremely simplified. Furthermore, because it is not necessary to solder or to attach extra lead wire to the circumferential side wall of the horn, the oscillation of the horn is not adversely affected by the (possibly hard to adequately control) weight of the mass of such solder.

Although the present invention has been shown and described with reference to the preferred embodiments thereof, and in terms of the illustrative drawings, it should not be considered as limited thereby. Various possible modifications, omissions, and alterations could be conceived of by one skilled in the art to the form and the content of any particular embodiment, without departing from the scope of the present invention. Therefore it is desired that the scope of the present invention, and of the protection sought to be granted by Letters Patent, should be defined not by any of the perhaps purely fortuitous details of the shown preferred embodiments, or of the drawings, but solely by the scope of the appended claims, which follow.

What is claimed is:

1. An oscillation apparatus for atomizing a liquid in an ultrasonic atomizing inhaler, said apparatus comprising:

an oscillation element having a liquid receiving region and an atomization region, said liquid receiving region and said atomization region having different fundamental frequencies of vibration; and a drive means for exciting said oscillation element to vibrate ultrasonically, said drive means having a driving frequency substantially equivalent to a resonant frequency of said atomization region, said drive means causing said atomization region to vibrate with a large amplitude and said liquid receiving region to vibrate with a smaller amplitude, so that constant atomization of the liquid is obtained even if the liquid supply load on said oscillating element changes.

2. An oscillating construction for an ultrasonic atomizing inhaler according to claim 1, wherein said oscillation element is substantially disk-shaped.

3. An oscillating construction for an ultrasonic atomizing inhaler according to claim 2, wherein said regions of said plate shaped oscillation element have respective edges which are separated by different distances from a central point of said plate.

4. An oscillating construction for an ultrasonic atomizing inhaler according to claim 3, wherein said plate shaped oscillation element is shaped as a circular disk with two portions cut away by two chords.

5. An oscillating construction for an ultrasonic atomizing inhaler according to claim 4, wherein said two portions cut away by two chords are substantially diametrically opposite, on said plate shaped oscillation element.

6. An oscillating construction for an ultrasonic atomizing inhaler according to claim 1, wherein said disk shaped oscillation element has a hemispherical cut-out portion cut away by a chord.

7. An oscillating construction for an ultrasonic atomizing inhaler according to claim 1, further comprising a means for exciting said oscillation element so as to cause it to vibrate ultrasonically, selectable to either of two different frequencies.

* * * * *